(12) United States Patent
Richard et al.

(10) Patent No.: US 8,323,624 B2
(45) Date of Patent: Dec. 4, 2012

(54) S-TRIAZINE SUNSCREENS BEARING HINDERED PARA-AMINOBENZALMA-LONATE/PARA-AMINOBENZALMALON-AMIDE AND AMINOBENZOATE/ AMINOBENZAMIDE SUBSTITUENTS

(75) Inventors: Herve Richard, Villepinte (FR); Catherine Lejuste, Le Vesinnet (FR)

(73) Assignee: L'Oreal, Paris (FR)

( * ) Notice: Subject to any disclaimer, the term of this patent is extended or adjusted under 35 U.S.C. 154(b) by 1038 days.

(21) Appl. No.: 11/214,865

(22) Filed: Aug. 31, 2005

(65) Prior Publication Data

US 2006/0045859 A1  Mar. 2, 2006

Related U.S. Application Data

(60) Provisional application No. 60/614,210, filed on Sep. 30, 2004.

(30) Foreign Application Priority Data

Sep. 2, 2004  (FR) ..................... 04 09292

(51) Int. Cl.
| | |
|---|---|
| A61K 8/00 | (2006.01) |
| A61K 8/18 | (2006.01) |
| A61Q 17/04 | (2006.01) |
| C07D 403/00 | (2006.01) |
| C07D 251/54 | (2006.01) |
| C07D 251/18 | (2006.01) |
| C07D 251/48 | (2006.01) |

(52) U.S. Cl. ........... 424/59; 544/197; 544/198; 544/206
(58) Field of Classification Search .................... 424/59; 544/197, 198, 206
See application file for complete search history.

(56) References Cited

U.S. PATENT DOCUMENTS

| | | | |
|---|---|---|---|
| 5,236,698 A | 8/1993 | Richard et al. | |
| 6,509,008 B1 | 1/2003 | Candau | |
| 6,517,742 B1 * | 2/2003 | Richard et al. ............... | 252/401 |
| 2006/0002872 A1 | 1/2006 | Candau et al. | |

FOREIGN PATENT DOCUMENTS

| | | |
|---|---|---|
| EP | 0 507 691 | 10/1992 |
| EP | 0 841 341 | 5/1998 |
| EP | 1 269 980 | 1/2003 |
| EP | 1 269 980 A1 | 1/2003 |
| FR | 2 674 850 A1 | 10/1992 |
| JP | 2006-16397 A | 1/2006 |
| JP | 2006-16398 A | 1/2006 |

OTHER PUBLICATIONS

French Search Report corresponding to FR 04/09292, issued on Apr. 1, 2005, 1 page.
Notice of Reasons for Rejection issued in Japanese Patent Application No. 2005-253652 dated May 5, 2007.

* cited by examiner

*Primary Examiner* — Mina Haghighatian
*Assistant Examiner* — Luke Karpinski
(74) *Attorney, Agent, or Firm* — Buchanan Ingersoll & Rooney PC

(57) ABSTRACT

Novel s-triazine sunscreens have the structural formula (I):

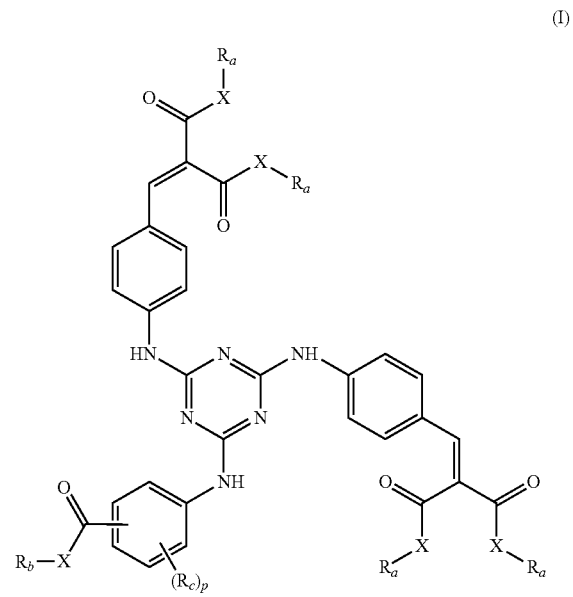

and are formulated into cosmetic/dermatological photoprotective compositions useful for photoprotecting keratinous substances against the damaging effects of UV-radiation.

14 Claims, No Drawings

S-TRIAZINE SUNSCREENS BEARING HINDERED PARA-AMINOBENZALMALONATE/PARA-AMINOBENZALMALONAMIDE AND AMINOBENZOATE/AMINOBENZAMIDE SUBSTITUENTS

CROSS-REFERENCE TO PRIORITY/PROVISIONAL APPLICATIONS

This application claims priority under 35 U.S.C. §119 of FR 04/09292, filed Sep. 2, 2004, and of provisional application Ser. No. 60/614,210, filed Sep. 30, 2004, each hereby expressly incorporated by reference and each assigned to the assignee hereof.

BACKGROUND OF THE INVENTION

1. Technical Field of the Invention

The present invention relates to novel s-triazine compounds bearing two substituents selected from among hindered para-aminobenzalmalonate and para-aminobenzalmalonamide groups and an aminobenzoate or aminobenzamide substituent and to their applications in cosmetics as sunscreen agents active in the region of UV radiation.

The present invention also relates to photoprotective compositions comprising such novel s-triazine compounds as sunscreen agents active in the region of UV radiation.

2. Description of Background and/or Related and/or Prior Art

It is known that radiation with wavelengths of from 280 nm to 400 nm makes possible browning of the human epidermis and that radiation with wavelengths of from 280 to 320 nm, known under the name of UV-B radiation, causes erythemas and skin burns which may be harmful to the development of natural tanning.

It is also known that UV-A rays, with wavelengths of from 320 to 400 nm, which cause browning of the skin, are capable of bringing about a detrimental change in the latter, in particular in the case of sensitive skin and/or of skin continually exposed to solar radiation. UV-A rays bring about in particular a loss of elasticity of the skin and the appearance of wrinkles, resulting in premature cutaneous aging. They promote the triggering of the erythemal reaction or accentuate this reaction in certain individuals and can even be the cause of phototoxic or photoallergic reactions. Thus, for aesthetic and cosmetic reasons, such as the retention of the natural elasticity of the skin, individuals increasingly desire to control the effect of UV-A radiation on their skin. The term "sun protection factor" is understood to mean the ratio of the irradiation time necessary to reach the erythemogenic threshold in the presence of the screening agent tested to the irradiation time necessary to reach the same threshold in the absence of screening agent.

It is therefore desirable to have available compounds capable of absorbing the entire range of UV radiation, both UV-B and UV-A rays.

In addition to their power in screening out UV-B and UV-A radiation, the desired photoprotective compounds must also exhibit good cosmetic properties, good solubility in conventional solvents and in particular in fatty substances, such as oils and fats, and good resistance to water and to perspiration (persistence) and very good photostability.

Mention may in particular be made, among all of the compounds which have been recommended for this purpose, of the s-triazine derivatives carrying para-aminobenzalmalonate substituents disclosed in EP-0,507,691 and EP-0,841,341, assigned to the assignee hereof. However, these compounds possess a photochemical stability and a solubility in conventional solvents which are not yet entirely satisfactory.

SUMMARY OF THE INVENTION

A novel family of s-triazine derivatives has now been developed possessing two substituents selected from among hindered para-aminobenzalmalonate and para-aminobenzalmalonamide groups and an aminobenzoate or aminobenzamide substituent, said novel s-triazine compounds having good absorbent properties in the complete range of the UV-A rays and a significant contribution in the region of the UV-B rays and a photostability and a solubility which are markedly improved with respect to the s-triazine derivatives grafted by para-aminobenzalmalonates of the prior art indicated above.

The present invention therefore features a novel family of s-triazine derivatives possessing two substituents selected from among hindered para-aminobenzalmalonate and para-aminobenzalmalonamide groups and an aminobenzoate or aminobenzamide substituent present in the formula (I) set forth below.

This invention also features cosmetic or dermatological compositions useful for the photoprotection of keratinous substances comprising, in a physiologically suitable medium, at least one compound of formula (I).

The term "physiologically acceptable medium" means a nontoxic medium capable of being applied to the skin, lips, hair, eyelashes, eyebrows or nails. The compositions of the invention can constitute, in particular, cosmetic or dermatological compositions.

The compounds in accordance with the present invention have the following structural formula (I):

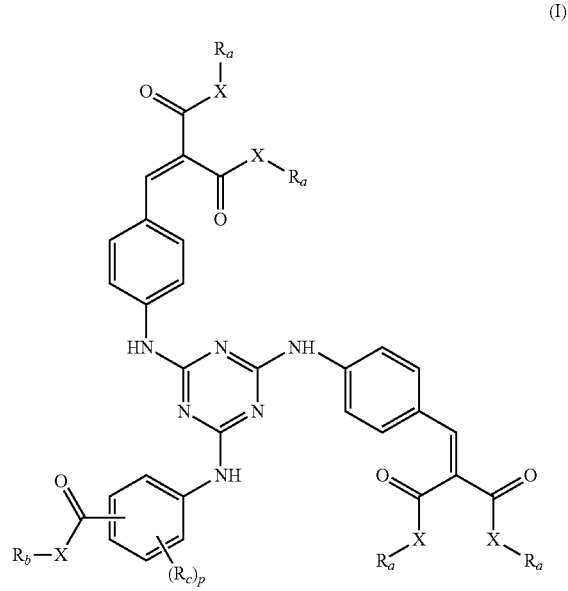

in which:
the radicals X, which may be identical or different, are each —O— or —$NR_6$—; the radicals $R_a$, which may be identical or different, are each a radical of formula (II):

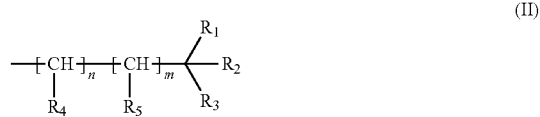

in which:

the radicals $R_1$ and $R_2$, which may be identical or different, are each a linear or branched $C_1$-$C_8$ alkyl radical, with the proviso that $R_1$ and $R_2$ can together form a $C_5$-$C_8$ ring member, optionally substituted by 1, 2 or 3 linear or branched $C_1$-$C_4$ alkyl radical(s), the radicals $R_3$, $R_4$ and $R_5$, which may be identical or different, are each a hydrogen atom or a linear or branched $C_1$-$C_4$ alkyl radical;

n has the value 0 or 1;

m has the value 0 or 1;

with the proviso that:

(i) when n=1 and $R_4$ is hydrogen, then m is equal to 0 and, (ii) when $R_1$ and $R_2$ together form a $C_5$-$C_8$ ring, then the sum n+m is other than 2;

the radical $R_6$ is hydrogen or a $C_1$-$C_8$ alkyl radical;

the radical $R_b$ is a linear or branched and optionally unsaturated $C_1$-$C_{20}$ alkyl radical, a $C_5$-$C_{12}$ cycloalkyl radical optionally substituted by 1 to 3 linear or branched $C_1$-$C_4$ alkyl radicals, the —(CH$_2$CHR$_7$—O)$_q$R$_8$ radical or the —CH$_2$—CH(OH)—CH$_2$—O—R$_8$ radical;

the radical $R_7$ is hydrogen or methyl;

the radical $R_8$ is hydrogen or a $C_1$-$C_8$ alkyl radical;

g=1-20;

the COXR$_b$ group can be in the ortho, meta or para position with respect to the amino group;

the radical $R_c$ is a saturated or unsaturated and linear or branched $C_1$-$C_{20}$ alkyl radical, the OH radical or a linear or branched $C_1$-$C_{20}$ alkoxy radical; and p is equal to 0, 1 or 2.

DETAILED DESCRIPTION OF BEST MODE AND SPECIFIC/PREFERRED EMBODIMENTS OF THE INVENTION

In the above formula (I), the alkyl radicals can be selected in particular from among the methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The alkyl radical which is particularly preferred is the methyl radical.

The cycloalkyl radicals can be selected in particular from among the cyclopentyl, cyclohexyl and cycloheptyl radicals. The cycloalkyl radical which is particularly preferred is the cyclohexyl radical. These radicals can be substituted by $C_1$-$C_4$ alkyl radicals preferably selected from among methyl, isopropyl and tert-butyl.

Mention will be made, among the preferred compounds of formula (I), of those for which the two following conditions are combined:
(a) n=m=0 and
(b) $R_1$, $R_2$ and $R_3$ are each a $C_1$-$C_4$ alkyl radical and more particularly methyl or else $R_3$ is hydrogen and $R_1$ and $R_2$ together form a $C_5$-$C_8$ ring member optionally substituted by one or two alkyl radicals and more particularly cyclohexyl.

Mention will also be made, among the preferred compounds of formula (I), of those for which the two following conditions are combined:
(a) n=1 and $R_4$ is an alkyl radical, in particular methyl, or m=1 and $R_5$ is an alkyl radical, in particular methyl, and
(b) $R_1$ and $R_2$ are each a $C_1$-$C_4$ alkyl radical and more particularly methyl.

Among the compounds of formula (I) which are more particularly preferred, are those compounds of the following formulae (1) to (10):

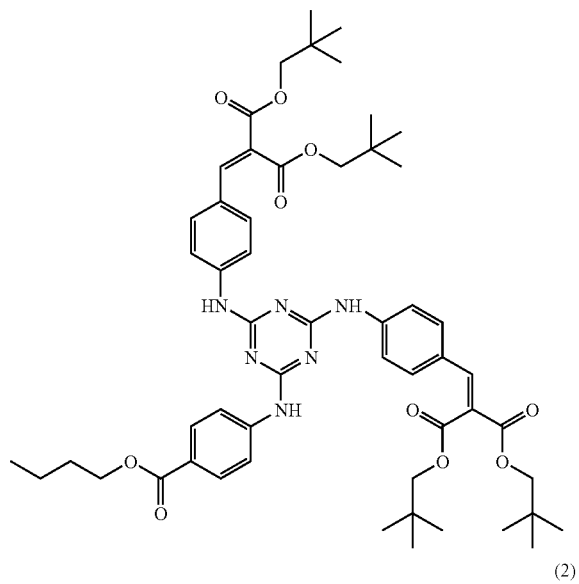

(1)

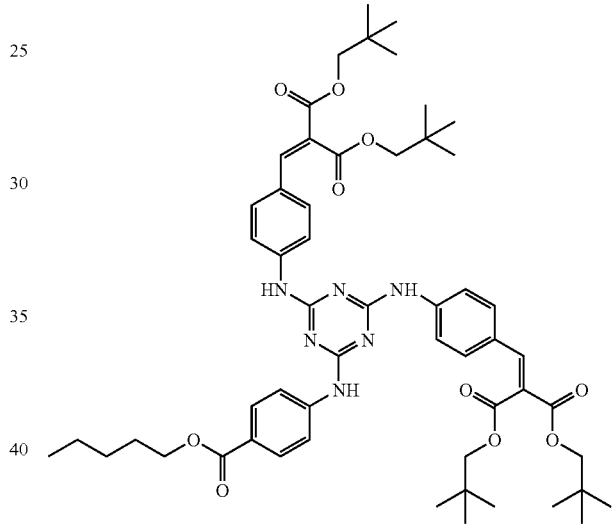

(2)

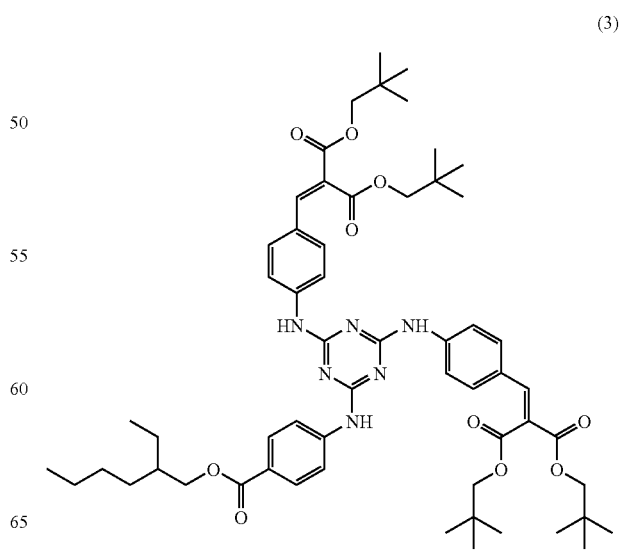

(3)

-continued
(4)
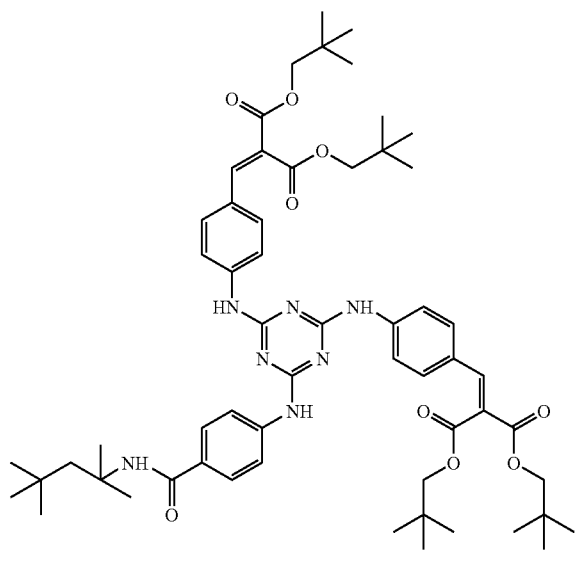
(5)
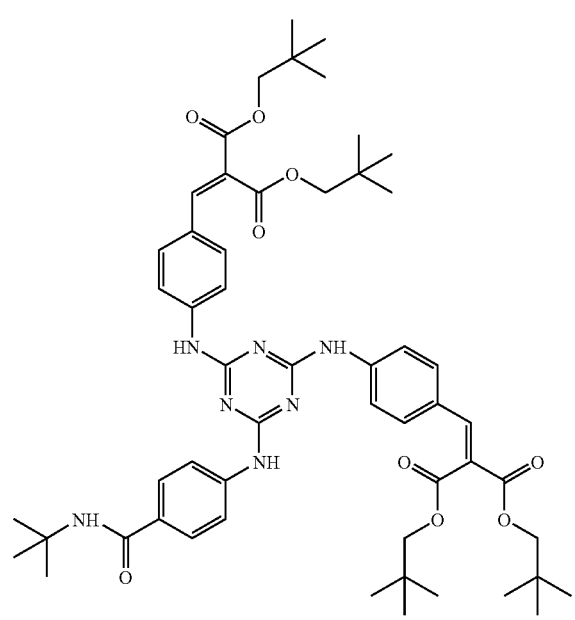
(6)
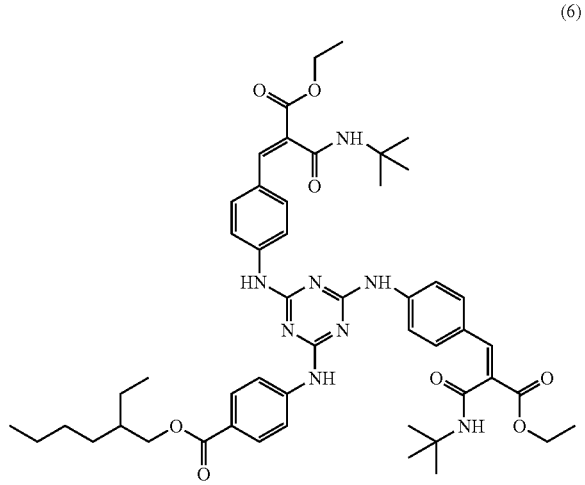
-continued
(7)
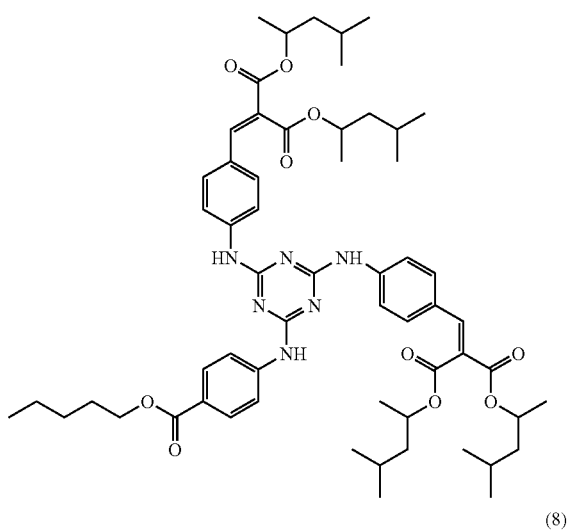
(8)
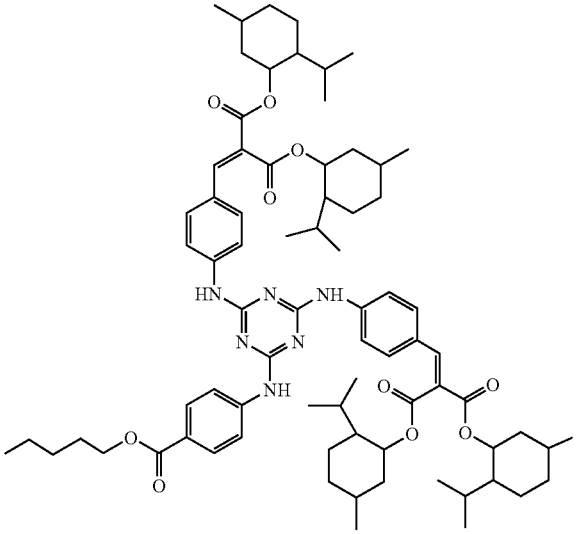
(9)
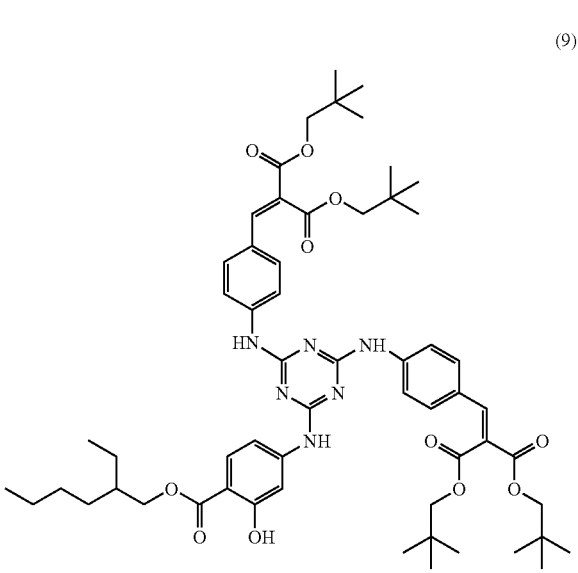

-continued (10)

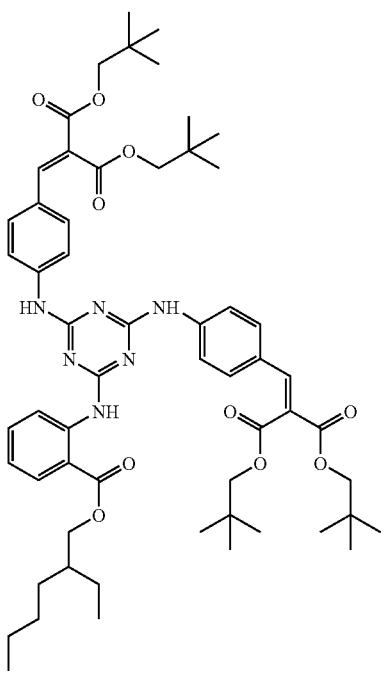

Among these compounds, particularly preferred is 2,4-bis(dineopentyl 4'-aminobenzalmalonate)-6-(butyl 4"-aminobenzoate)-s-triazine of formula (1).

The compounds of formula (I) can be prepared according to the following scheme (A):

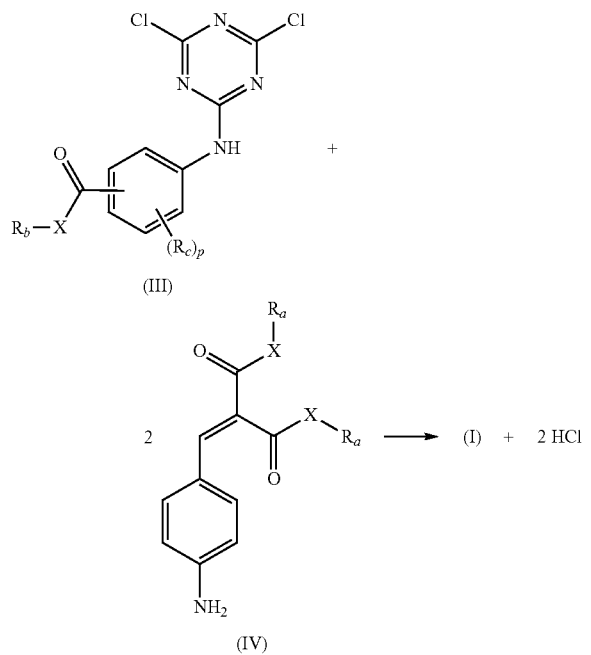

in which $R_a$, X, $R_b$, $R_c$ and p have the definitions of the formula (I) above.

The above reactions can optionally be carried out in the presence of a solvent (for example: toluene, xylene or 1,2-dichloroethane) at a temperature of from 0° C. to 250° C., more particularly from 5° C. to 150° C. They can also be carried out using microwave radiation in the presence or absence of a solvent (for example: toluene, xylene or 1,2-dichloroethane) or in the presence or absence of 10% of graphite, at a temperature of 50 to 150° C., at a power of 50-150 watts for a period of time of 10 to 30 minutes.

The compounds of formula (III) can be prepared according to known methods, for example disclosed in EP-0,507,691, also assigned to the assignee hereof.

The present invention also features cosmetic or dermatological compositions comprising, formulated into a physiologically acceptable medium, at least one compound of formula (I).

The compounds of formula (I) are generally present in the compositions of the invention in proportions of from 0.01% to 20% by weight, preferably from 0.1% to 10% by weight, with respect to the total weight of the composition.

The compositions in accordance with the invention can additionally comprise other supplementary UV screening agents which are active in the UV-A and/or UV-B regions. The additional photoprotective agents are generally present in the compositions according to the invention in proportions ranging from 0.01 to 20% by weight, with respect to the total weight of the composition, preferably ranging from 0.1 to 10% by weight, with respect to the total weight of the composition.

The compositions according to the invention can also comprise agents for the artificial tanning and/or browning of the skin (self-tanning agents) and more particularly dihydroxyacetone (DHA). These are preferably present in amounts ranging from 0.1 to 10% by weight, with respect to the total weight of the composition.

The compositions in accordance with the present invention can additionally comprise conventional cosmetic adjuvants selected in particular from among fatty substances, organic solvents, ionic or nonionic and hydrophilic or lipophilic thickeners, softeners, humectants, opacifiers, stabilizers, emollients, silicones, antifoaming agents, fragrances, preservatives, anionic, cationic, nonionic, zwitterionic or amphoteric surfactants, active principles, fillers, polymers, propellants, basifying or acidifying agents or any other ingredient commonly used in the cosmetic and/or dermatological field.

The fatty substances can be composed of an oil or a wax or their mixtures. The term "oil" is understood to mean a compound which is liquid at ambient temperature. The term "wax" is understood to mean a compound which is solid or substantially solid at ambient temperature and which has a melting point generally of greater than 35° C.

Mention may be made, as oils, of mineral oils (liquid paraffin); vegetable oils (sweet almond, macadamia, blackcurrant seed or jojoba oil); synthetic oils, such as perhydrosqualene, fatty alcohols, acids or esters (such as the $C_{12}$-$C_{15}$ alkyl benzoate marketed under the trademark "Finsolv TN" by Witco, octyl palmitate, isopropyl lanolate or triglycerides, including those of capric/caprylic acids), or oxyethylenated or oxypropylenated fatty esters and ethers; silicone oils (cyclomethicone, polydimethylsiloxanes or PDMSs); fluorinated oils; or polyalkylenes.

Mention may be made, as waxy compounds, of paraffin wax, carnauba wax, beeswax or hydrogenated castor oil.

Mention may be made, among organic solvents, of lower alcohols and polyols. The latter can be selected from among glycols and glycol ethers, such as ethylene glycol, propylene glycol, butylene glycol, dipropylene glycol or diethylene glycol.

Mention may be made, as hydrophilic thickeners, of carboxyvinyl polymers, such as carbopols (carbomers) and Pemulens (acrylates/$C_{10}$-$C_{30}$ alkyl acrylate copolymer); polyacrylamides, such as, for example, the crosslinked copolymers marketed under the names Sepigel 305 (CTFA name: polyacrylamide/$C_{13-14}$ isoparaffin/laureth 7) or Simulgel 600 (CTFA name: acrylamide/sodium acryloyldimethyltaurate copolymer/isohexadecane/polysorbate 80) by Seppic; optionally crosslinked and/or neutralized polymers and copolymers of 2-acrylamido-2-methylpropanesulfonic acid, such as the poly(2-acrylamido-2-methylpropanesulfonic acid) marketed by Hoechst under the trademark "Hostacerin AMPS" (CTFA name: ammonium polyacryldimethyltauramide); cellulose derivatives, such as hydroxyethylcellulose; polysaccharides and in particular gums, such as xanthan gum; and their mixtures.

Mention may be made, as lipophilic thickeners, of modified clays, such as hectorite and its derivatives, such as the products marketed under the Bentone names.

Mention may be made, among the active principles, of:
  agents for combating pollution and/or agents for combating free radicals;
  depigmenting agents and/or propigmenting agents;
  antiglycation agents;
  NO-synthase inhibitors;
  agents which stimulate the synthesis of dermal or epidermal macromolecules and/or which prevent their decomposition;
  agents which stimulate the proliferation of fibroblasts;
  agents which stimulate the proliferation of keratinocytes;
  muscle relaxants;
  tightening agents;
  desquamating agents;
  moisturizing agents;
  anti-inflammatories;
  agents which act on the energy metabolism of the cells;
  insect repellents;
  substance P or CRGP antagonists.

Of course, one skilled in the art will take care to choose the optional additional compound or compounds mentioned above and/or their amounts so that the advantageous properties intrinsically associated with the compositions in accordance with the invention are not, or not substantially, detrimentally affected by the envisaged addition or additions.

The compositions according to the invention can be prepared according to techniques well known to this art, in particular those intended for the preparation of emulsions of oil-in-water or water-in-oil type. They can be provided in particular in the form of a simple or complex emulsion (O/W, W/O, O/W/O or W/O/W), such as a cream or milk, in the form of a gel or of a cream gel or in the form of a lotion, powder or solid stick and can optionally be packaged as an aerosol and be provided in the form of a foam or spray.

Preferably, the compositions according to the invention are provided in the form of an oil-in-water or water-in-oil emulsion.

The emulsions generally comprise at least one emulsifier selected from among amphoteric, anionic, cationic or nonionic emulsifiers, used alone or as a mixture. The emulsifiers are appropriately selected according to the emulsion to be obtained (W/O or O/W).

Mention may be made, as emulsifying surfactants which can be used for the preparation of the W/O emulsions, of, for example, sorbitan alkyl esters or ethers, glycerol alkyl esters or ethers or sugar alkyl esters or ethers; or silicone surfactants, such as dimethicone copolyols, for example the mixture of cyclomethicone and of dimethicone copolyol marketed under the name "DC 5225 C" by Dow Corning, and alkyl dimethicone copolyols, for example lauryl methicone copolyol, marketed under the name "Dow Corning 5200 Formulation Aid" by Dow Corning, cetyl dimethicone copolyol, for example the product marketed under the name Abil EM 90® by Goldschmidt, and the mixture of cetyl dimethicone copolyol, of polyglyceryl (4 mol) isostearate and of hexyl laurate marketed under the name Abil WE 09 by Goldschmidt. One or more coemulsifiers which can advantageously be selected from the group consisting of polyol alkyl esters can also be added thereto. Mention may in particular be made, as polyol alkyl esters, of glycerol and/or sorbitan esters and, for example, polyglyceryl isostearate, such as the product marketed under the name Isolan GI 34 by Goldschmidt, sorbitan isostearate, such as the product marketed under the name Arlacel 987 by ICI, the isostearate of sorbitan and of glycerol, such as the product marketed under the name Arlacel 986 by ICI, and their mixtures.

Mention may be made, for the O/W emulsions, of, for example, as emulsifiers, nonionic emulsifers, such as oxyalkylenated (more particularly polyoxyethylenated) esters of fatty acids and of glycerol; oxyalkylenated esters of fatty acids and of sorbitan; oxyalkylenated (oxyethylenated and/or oxypropylenated) esters of fatty acids; oxyalkylenated (oxyethylenated and/or oxypropylenated) ethers of fatty alcohols; sugar esters, such as sucrose stearate; fatty alcohol and sugar ethers, in particular alkyl polyglucosides (APG), such as decyl glucoside and lauryl glucoside, marketed, for example, by Henkel under the respective names Plantaren 2000 and Plantaren 1200, cetearyl glucoside, optionally as a mixture with cetearyl alcohol, marketed, for example, under the name Montanov 68 by Seppic, under the name Tegocare CG90 by Goldschmidt and under the name Emulgade KE3302 by Henkel, and arachidyl glucoside, for example in the form of the mixture of arachidyl and behenyl alcohols and of arachidyl glucoside marketed under the name Montanov 202 by Seppic. According to a specific embodiment of the invention, the mixture of the alkyl polyglucoside as defined above with the corresponding fatty alcohol can be in the form of a self-emulsifying composition, as disclosed, for example, in the document WO-A-92/06778.

When it is an emulsion, the aqueous phase of the latter can comprise a nonionic vesicular dispersion prepared according to known methods (Bangham, Standish and Watkins, *J. Mol. Biol.*, 13, 238 (1965), FR-2,315,991 and FR-2,416,008).

The compositions according to the invention have applications in a large number of treatments, in particular cosmetic treatments (regime or regimen), of the skin, lips and hair, including the scalp, in particular for the protection and/or the care of the skin, lips and/or hair and/or for making up the skin and/or lips.

The present invention also features the use of the subject compositions as defined above in the manufacture of products for the cosmetic treatment of the skin, lips, nails, hair, eyelashes, eyebrows and/or scalp, in particular care products and makeup products.

The cosmetic compositions according to the invention can, for example, be topically applied as care products and/or sun protection products for the face and/or body with a liquid to semi-liquid consistency, such as milks, more or less smooth creams, cream gels or pastes. They can optionally be packaged as an aerosol and be provided in the form of a foam or spray.

The compositions according to the invention in the form of vaporizable fluid lotions are applied to the skin or hair in the form of fine particles by means of pressurization devices. The devices in accordance with the invention are well known to one skilled in the art and comprise non-aerosol pumps or "atomizers", aerosol containers comprising a propellant, and aerosol pumps using compressed air as propellant. The latter are disclosed in U.S. Pat. Nos. 4,077,441 and 4,850,517, hereby incorporated by reference.

The compositions packaged as an aerosol in accordance with the invention generally comprise conventional propellants, such as, for example, hydrofluoro compounds, dichlorodifluoromethane, difluoroethane, dimethyl ether, isobutane, n-butane, propane or trichlorofluoromethane. They are preferably present in amounts ranging from 15 to 50% by weight with respect to the total weight of the composition.

This invention also features formulating a compound of formula (I) as defined above into cosmetic or dermatological compositions as agent for screening out UV radiation.

This invention also features formulating a compound of formula (I) as defined above into cosmetic compositions as agent for controlling the variation in the color of the skin due to UV radiation.

And this invention also features the use of a compound of formula (I) as defined above as photostabilizing agent for synthetic polymers, such as plastics, or for glasses, in particular spectacle glasses or contact lenses.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

Synthesis of 2,4-bis(dineopentyl 4'-aminobenzalmalonate)-6-(butyl 4''-aminobenzoate)-s-triazine of Formula (1)

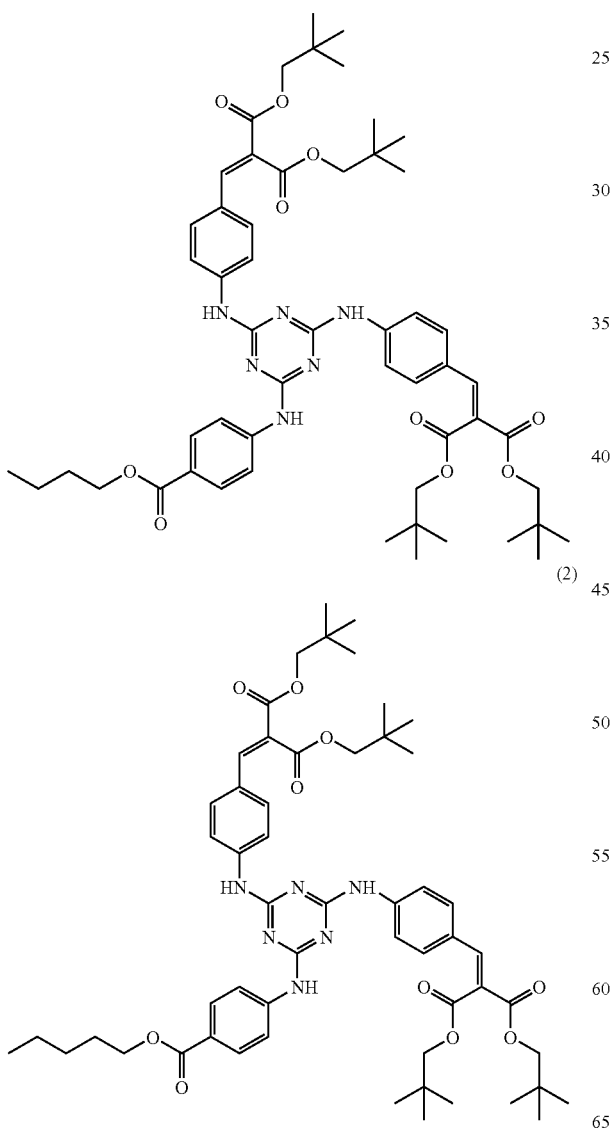

First Stage: Preparation of 2,4-dichloro-6-(butyl 4'-aminobenzoate)-s-triazine:

Cyanuric chloride (20.7 g, 0.112 mol) is dissolved at 0-5° C. in 250 ml of acetone in a reactor. A solution of butyl para-aminobenzoate (21.7 g, 0.112 mol) dissolved in 70 ml of acetone is added thereto dropwise at 0-5° C. over 1 hour. Subsequently, sodium bicarbonate (9.4 g, 0.112 mol) dissolved in 70 ml of water is added thereto. The heterogeneous mixture is left at a temperature of 0-5° C. for 2 hours. The precipitate formed is filtered off and then washed with water and with acetone. After drying under vacuum, 37.2 g (Yield 97%) of 2,4-dichloro-6-(butyl 4'-aminobenzoate)-s-triazine are obtained in a form of a white powder:

UV (Ethanol/DMSO): $\lambda_{max}$=298 nm, $E_{1\%}$=940, which is used as is in the following stage.

Second Stage: Synthesis of the Derivative of Example 1:

A mixture of the preceding product (7.41 g, 0.0213 mol) and of dineopentyl para-aminobenzalmalonate (14.66 g, 0.0422 mol) in suspension in 60 ml of toluene is heated at reflux for 7 hours 30 minutes while sparging with nitrogen. The mixture is cooled and dichloromethane is added. The organic phase is washed with a saturated sodium bicarbonate solution and then with water. The organic phase is dried and then concentrated under reduced pressure. The orangey oil obtained (17.8 g) is subjected to separation on a silica column (eluent: Heptane/EtOAc 85:15). Clean fractions in the form of pale yellow flakes of the derivative of Example 1 are recovered (8.72 g, Yield 43%).

UV (Ethanol):
$\lambda$=370 nm, $E_{1\%}$=623; $\lambda_{max}$=347 nm, $E_{1\%}$=847; $\lambda$=300 nm, $E_{1\%}$=432.

Example 2

Synthesis of 2,4-bis(dineopentyl 4'-aminobenzalmalonate)-6-(amyl 4''-aminobenzoate)-s-triazine of Formula (2)

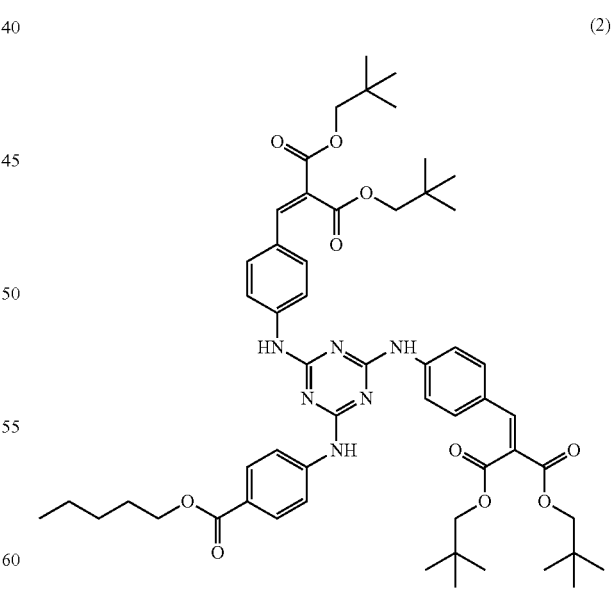

First Stage: Preparation of 2,4-dichloro-6-(amyl 4'-aminobenzoate)-s-triazine:

Cyanuric chloride (14.7 g, 0.0796 mol) is dissolved at 10° C. in 200 ml of dioxane in a reactor. A solution of amyl para-aminobenzoate (16.5 g, 0.0796 mol) dissolved in 60 ml of dioxane and a solution of potassium carbonate (5.5 g, 0.0398 mol) dissolved in 30 ml of water are simultaneously added thereto dropwise at 10° C. over 1 hour. The heterogeneous mixture is left at a temperature of 10° C. for 2 hours. Approximately 300 ml of water are added and the precipitate formed is filtered off and then washed with water. After drying under vacuum, 26.4 g (Yield 93%) of 2,4-dichloro-6-(amyl 4'-aminobenzoate)-s-triazine are obtained in the form of a white powder which is used as is in the following state.

Second Stage: Synthesis of the Derivative of Example 2:

The intimately mixed mixture of the preceding product (0.103 g, 0.29×10$^{-3}$ mol), of dineopentyl para-aminobenzalmalonate (0.2 g, 0.58×10$^{-3}$ mol) and of sodium bicarbonate (0.049 g, 0.58×10$^{-3}$ mol) is left in a CEM Discover microwave system for 10 minutes at a temperature of 150° C. and under a power of 150 watts. The amorphous solid formed is extracted with dichloromethane. The organic phase is washed 3 times with water, is dried and is then concentrated under reduced pressure. The yellow oil obtained is subjected to separation on a silica column (eluent: Heptane/EtOAc 80/20). Clean fractions in the form of a pale yellow paste of the derivative of Example 2 are recovered (36 mg, Yield 15%):
UV (Ethanol):
$\lambda$=375 nm, $E_{1\%}$=610; $\lambda_{max}$=347 nm, $E_{1\%}$=834; $\lambda$=300 nm, $E_{1\%}$=425.

Example 3

Synthesis of 2,4-bis(dineopentyl 4'-aminobenzalmalonate)-6-(2-ethylhexyl 4''-aminobenzoate)-s-triazine of Formula (3)

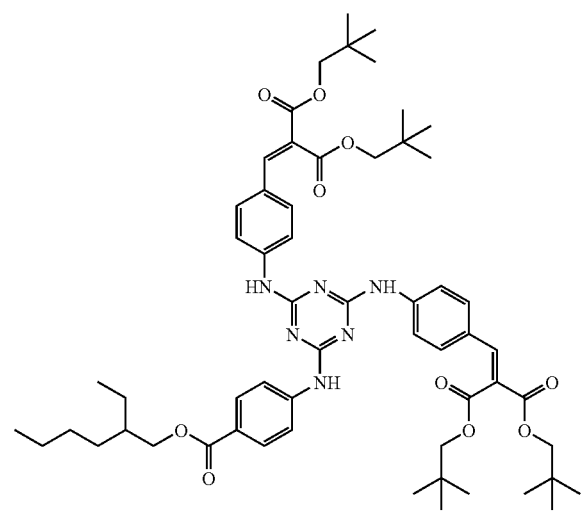

First Stage: Preparation of 2,4-dichloro-6-(2-ethylhexyl 4'-aminobenzoate)-s-triazine:

Cyanuric chloride (18.4 g, 0.1 mol) is dissolved at 0-5° C. in 150 ml of acetone in a reactor. Sodium bicarbonate (10.6 g, 0.1 mol) is added thereto and then a solution of 2-ethylhexyl para-aminobenzoate (24.9 g, 0.1 mol) dissolved in 150 ml of acetone is added dropwise over 10 minutes at a temperature of less than 10° C. The heterogeneous mixture is subsequently left for 3 hours at the laboratory temperature. 500 ml of water are poured onto the mixture. The precipitate formed is filtered off and then washed with water. After drying under vacuum, 38 g of an off-white solid are obtained. After recrystallizing this solid from 1,2-dichloroethane, 25.2 g (Yield 63%) of 2,4-dichloro-6-(2-ethylhexyl 4'-aminobenzoate)-s-triazine are obtained in the form of a white powder:

UV (Ethanol/DMSO): $\lambda_{max}$=291 nm, $E_{1\%}$=732, which is used as is in the following stage.

Second Stage: Synthesis of the Derivative of Example 3:

A mixture of the preceding product (1.14 g, 2.87×10$^{-3}$ mol) and of dineopentyl para-aminobenzalmalonate (2.2 g, 6.33×10$^{-3}$ mol) in suspension in 35 ml of toluene is heated at reflux for 10 hours 30 minutes while sparing with nitrogen. The mixture is cooled and dichloromethane is added. The organic phase is washed with a saturated sodium bicarbonate solution and then with water. The organic phase is dried and then concentrated under reduced pressure. The orangey oil obtained (2.6 g) is subjected to separation on a silica column (eluent: Heptane/EtOAc 85:15). Clean fractions in the form of pale yellow flakes of the derivative of Example 3 are recovered (1.17 g, Yield 40%):
UV (Ethanol):
$\lambda$=370 nm, $E_{1\%}$=575; $\lambda_{max}$=342 nm, $E_{1\%}$=880; $\lambda$=300 nm, $E_{1\%}$=448.

Example 4

Synthesis of 2,4-bis(dineopentyl 4'-aminobenzalmalonate)-6-(tert-octyl-4''-aminobenzamide)-s-triazine of Formula (4)

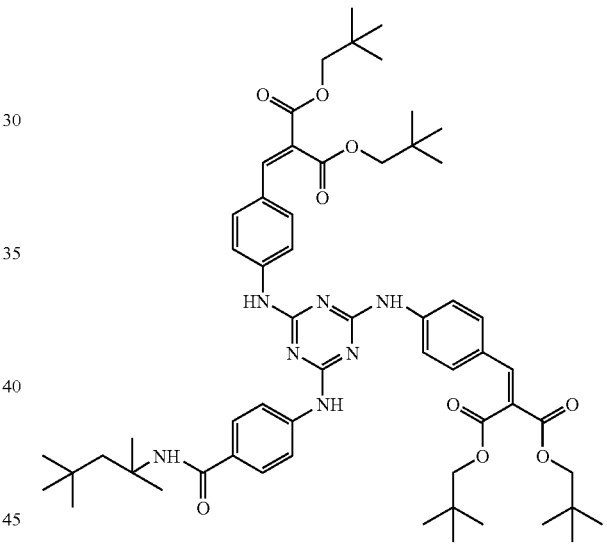

First Stage: Preparation of 4-nitro-N-(tert-octyl)benzamide:

tert-Octylamine (51.7 g, 0.4 mol) and triethyamine (61.2 ml, 0.44 mol) are introduced into 260 ml of dichloroethane in a reactor. The mixture is heated to 70° C. and then 4-nitrobenzoyl chloride (77.9 g, 0.42 mol) is added in small portions over 50 minutes. The mixture is heated at reflux for 4 hours. The mixture is poured onto ice-cold water; extraction is carried out with dichloromethane, the extract is dried and the solvent is evaporated. The beige precipitate obtained is recrystallized from a mixture of isopropyl ether and ethanol (ratio 10:1). After drying under vacuum, 84.6 g (Yield 76%) of 4-nitro-N-(tert-octyl)benzamide are obtained in the form of an off-white powder which is used as is in the following stage.

Second Stage: Preparation of 4-amino-N-(tert-octyl)-benzamide:

4-Nitro-N-(tert-octyl)benzamide (30 g, 0.108 mol) dissolved in 200 ml of ethyl acetate is hydrogenated for 1 hour 15 minutes at a temperature of 70-75° C. in a 500 ml hydrogenator in the presence of 4.8 g of 10% palladium-on-charcoal comprising 50% water as catalyst (hydrogen pressure: 8-10 bar). After filtering, concentrating the solvent and drying under vacuum, 20.4 g (Yield: 76%) of 4-amino-N-(tert-octyl) benzamide are obtained in the form of a pale yellow powder which is used as is in the following stage.

Third Stage: Preparation of N-(tert-octyl)-4-[(4,6-dichloro-1,3,5-triazin-2-yl)amino]benzamide:

Cyanuric chloride (3.7 g, 0.0201 mol) is dissolved at 10° C. in 70 ml of dioxane in a reactor. A solution of the product from the preceding stage (5 g, 0.0201 mol) dissolved in 100 ml of dioxane and a solution of potassium carbonate (1.4 g, 0.03 mol) dissolved in 20 ml of water are simultaneously added thereto dropwise at 10° C. over 1 hour. The heterogeneous mixture is left at a temperature of 10° C. for 2 hours. Approximately 300 ml of water are added and the precipitate formed is filtered off and then washed with water. After drying under vacuum, 7.4 g (Yield 93%) of N-(tert-octyl)-4-[(4,6-dichloro-1,3,5-triazin-2-yl)amino]benzamide are obtained in the form of a white powder which is used as is in the following stage.

Fourth Stage: Synthesis of the Derivative of Example 4:

The intimately mixed mixture of the product from the preceding stage (0.29 g, 0.732×10$^{-3}$ mol), of dineopentyl para-aminobenzalmalonate (0.5 g, 1.44×10$^{-3}$ mol) and of sodium bicarbonate (0.14 g, 1.44×10$^{-3}$ mol) is left in a CEM Discover microwave system for 4 minutes at a temperature of 60° C. and under a power of 300 watts and then for 15 minutes at a temperature of 110° C. The amorphous solid formed is extracted with dichloromethane. The organic phase is washed 3 times with water, is dried and is then concentrated under reduced pressure. The orangey oil obtained is subjected to separation on a silica column (eluent: Heptane/EtOAc 75:25). Clean fractions in the form of a pale yellow oil are recovered, which oil solidifies to give the derivative of Example 5 (0.6 g, Yield 86%) in the form of a pale yellow powder:

UV (Ethanol):

$\lambda$=351 nm, $E_{1\%}$=763; $\lambda_{max}$=298 nm, $E_{1\%}$=369.

Example 5

Synthesis of 2,4-bis(dineopentyl 4'-aminobenzalmalonate)-6-(tert-butyl-4"-aminobenzamide)-s-triazine of Formula (5)

(5)

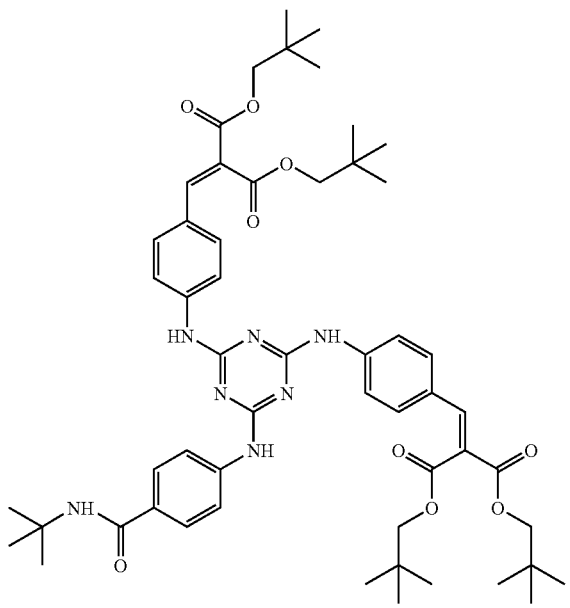

First Stage: Preparation of N-(tert-butyl)-4-nitrobenzamide:

4-Nitrobenzoyl chloride (18.9 g, 0.1 mol) dissolved in 60 ml of methylene chloride is added, over 30 minutes at a temperature of 0-5° C., to a solution of tert-butylamine (8.3 g, 0.112 mol) and of triethylamine (15.6 ml, 0.112 mol) dissolved in 170 ml of dichloromethane in a reactor. The reaction mixture is brought back to laboratory temperature and left stirring for 2 hours. The organic phase is washed twice with water and dried. After removing the solvent under reduced pressure, the solid obtained is recrystallized from isopropanol. 17.1 g (Yield: 77%) of N-(tert-butyl)-4-nitrobenzamide are obtained in the form of a pale yellow powder (m.p. 161-2° C.) which is used as is in the following stage.

Second Stage: Preparation of 4-amino-N-(tert-butyl)benzamide:

The preceding product (17.1 g, 0.077 mol) dissolved in 300 ml of isopropanol is hydrogenated for 30 minutes at a temperature of 60° C. in a 1 liter hydrogenator in the presence of 3 g of 5% palladium-on-charcoal as catalyst (hydrogen pressure: 7 bar). After filtering, concentrating the solvent and drying under vacuum, 13.2 g (Yield: 89%) of 4-amino-N-(tert-butyl)benzamide are obtained in the form of a pale grey powder (m.p. 123-4° C.) which is used as is in the following stage.

Third Stage: Preparation of N-(tert-butyl)-4-[(4,6-dichloro-1,3,5-triazin-2-yl)amino]benzamide:

Cyanuric chloride (11.71 g, 0.06 mol) is dissolved at 10° C. in 150 ml of dioxane in a reactor. A solution of the product from the preceding stage (11.53 g, 0.06 mol) dissolved in 60 ml of dioxane and a solution of potassium carbonate (6.3 g, 0.03 mol) dissolved in 30 ml of water are simultaneously added thereto dropwise at 10° C. over 1 hour. The heterogeneous mixture is left at a temperature of 10° C. for 2 hours. Approximately 300 ml of water are added and the precipitate formed is filtered off and then washed with water. After drying under vacuum, 18 g (Yield 88%) of N-(tert-butyl)-4-[(4,6-dichloro-1,3,5-triazin-2-yl)amino]benzamide are obtained in the form of a white powder (m.p. 256-7° C.) which is used as is in the following stage.

Fourth Stage: Synthesis of the Derivative of Example 5:

The intimately mixed mixture of the preceding product (1.5 g, 4.4×10$^{-3}$ mol), of dineopentyl para-aminobenzalmalonate (3 g, 8.8×10$^{-3}$ mol) and of sodium bicarbonate (0.37 g, 8.8×10$^{-3}$ mol) is left in a CEM Discover microwave system for 4 minutes at a temperature of 60° C. and under a power of 300 watts and then for 20 minutes at a temperature of 150° C. The amorphous solid formed is extracted with dichloromethane. The organic phase is washed 3 times with water, is dried and is then concentrated under reduced pressure. The brown oil obtained is subjected to separation on a silica column (eluent: Heptane/EtOAc 60:40). Clean fractions in the form of a pale yellow powder of the derivative of Example 5 are recovered (0.7 g, Yield 17%):

UV (Ethanol):
$\lambda=375$ nm, $E_{1\%}=420$; $\lambda_{max}=345$ nm, $E_{1\%}=813$; $\lambda=299$ nm, $E_{1\%}=420$.

Example 6

Synthesis of 2,4-bis(1,3-dimethylbutyl 4'-aminobenzalmalonate)-6-(amyl 4"-aminobenzoate)-s-triazine of Formula (7)

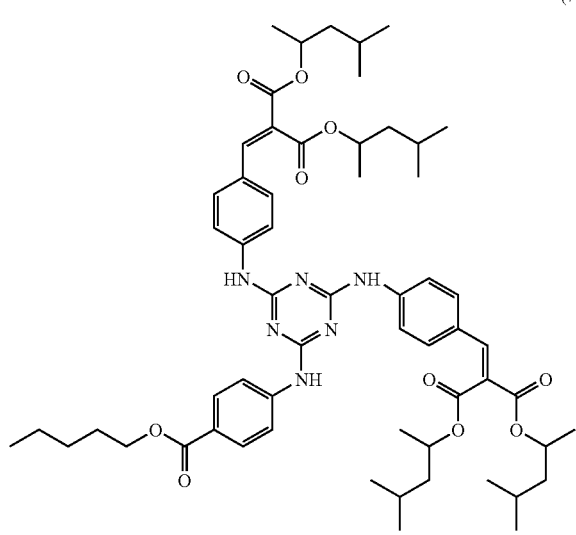

(7)

First Stage: Preparation of 1,3-dimethylbutyl malonate:

Malonic acid (72.8 g, 0.7 mol) and the alcohol 2-methyl-4-pentanol (286 g, 2.8 mol) are brought to reflux for 2 hours in 200 ml of toluene in the presence of 1.8 ml of concentrated sulfuric acid in a reactor surmounted by a Dean & Stark apparatus. The water formed is removed by azeotropic distillation. The organic phase is washed 3 times with water and is dried over sodium sulfate. The sodium sulfate is filtered off and the solvent is evaporated. The product obtained distils at 147° C. under 20 hPa. 160 g (Yield 79%) of 1,3-dimethylbutyl malonate are obtained in the form of a colorless oil which is used as is in the following stage.

Second Stage: Preparation of 1,3-dimethylbutyl 4-nitrobenzalmalonate:

p-Nitrobenzaldehyde (49.9 g, 0.33 mol) and 1,3-dimethylbutyl malonate (90 g, 0.33 mol) are placed in 150 ml of toluene in a round-bottomed flask equipped with a Dean & Stark apparatus surmounted by a reflux condenser and while sparging with nitrogen. The catalyst prepared in advance, acetic acid (1.9 ml) and piperidine (3.3 ml) in suspension in 4 ml of toluene, is added thereto. The mixture is brought to reflux with stirring for 7 hours 30 minutes and the water formed is removed via the Dean & Stark apparatus. Two further additions of the same amounts of catalyst were necessary. The cooled reaction mixture is poured into water and extracted with dichloromethane. The organic phase is washed with water, then dried and concentrated under reduced pressure. The red-brown oil obtained is chromatographed on a silica column (eluent: Heptane/EtOAc 97:3). 56.8 g (Yield 43%) of the clean fractions of 1,3-dimethylbutyl 4-nitrobenzalmalonate are recovered in the form of a yellow oil which is used as is in the following stage.

Third Stage: Preparation of 1,3-dimethylbutyl 4-aminobenzalmalonate:

The derivative from the preceding stage (56.8 g, 0.14 mol) is dispersed in 80 ml of acetic acid with stirring and sparging with nitrogen. 115 ml of water are added thereto. The mixture is heated to 50° C. Iron (78.2 g, 1.4 mol) is added thereto portionwise without exceeding a temperature of 55° C. (introduction time 1 hour). Subsequently, acetic acid (115 ml) is added dropwise without exceeding a temperature of 55° C. (introduction time 2 hours). The mixture is heated for a further 1 hour at 55° C. It is cooled, water is added and extraction is carried out twice with dichloromethane. The organic phase is washed with water, with a saturated sodium bicarbonate solution and with water and is then dried over sodium sulfate. After concentrating under reduced pressure, a red-brown oil is obtained and is purified by passing through a silica column (eluent: Heptane/EtOAc 85:15). It is recrystallized from a mixture of heptane and 1,2-dichloroethane. 22.5 g (Yield 43%) of the clean fractions of 1,3-dimethylbutyl 4-aminobenzalmalonate are recovered in the form of an orangey oil which is used as is in the following stage.

Fourth Stage: Synthesis of the Derivative of Example 6:

The intimately mixed mixture of the product from the preceding stage (0.5 g, $1.32\times10^{-3}$ mol), of the product from the first stage of Example 2 (0.235 g, $0.66\times10^{-3}$ mol) and of sodium bicarbonate (0.11 g, $1.32\times10^{-3}$ mol) is left in a CEM Discover microwave system for 4 minutes at a temperature of 60° C. and under a power of 300 watts and then for 25 minutes at a temperature of 110° C. The amorphous solid formed is extracted with dichloromethane. The organic phase is washed 3 times with water, is dried and is then concentrated under reduced pressure. The orangey oil obtained is subjected to separation on a silica column (eluent: Heptane/EtOAc 80:20). Clean fractions are recovered in the form of a yellow oil, which solidifies to give the derivative of Example 6 (0.4 g, Yield 57%) in the form of light-yellow flakes:

UV (Ethanol):
$\lambda=370$ nm, $E_{1\%}=500$; $\lambda_{max}=337$ nm, $E_{1\%}=800$; $\lambda=300$ nm, $E_{1\%}=411$.

Example 7

Synthesis of 2,4-bis(dimenthyl 4'-aminobenzalmalonate)-6-(amyl 4''-aminobenzoate)-s-triazine of Formula (8)

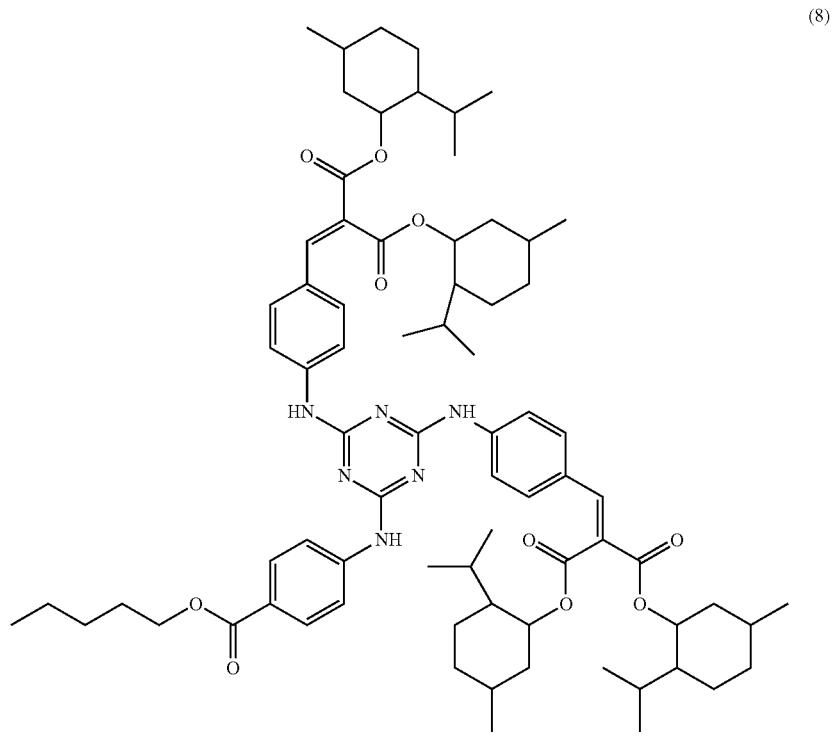

(8)

First Stage: Preparation of dimethyl malonate:

Malonic acid (22.2 g, 0.213 mol) and menthol (70 g, 0.448 mol) are brought to reflux for 6 hours in 100 ml of toluene in the presence of 2 ml of concentrated sulfuric acid in a reactor surmounted by a Dean & Stark apparatus. The water formed is removed by azeotropic distillation. The organic phase is washed 3 times with water and is dried over sodium sulfate. The excess menthol is removed by distillation under vacuum (140° C. under 0.6 hPa). The residue is treated with animal charcoal in isopropanol at reflux. After filtering, rinsing and evaporating the solvent, 61.8 g (Yield 76%) of dimethyl malonate are obtained in the form of a yellow oil which is used as is in the following stage.

Second Stage: Preparation of dimethyl 4-nitrobenzalmalonate:

p-Nitrobenzaldehyde (21.8 g, 0.144 mol) and dimethyl malonate (61 g, 0.16 mol) are placed in 100 ml of toluene in a round-bottomed flask equipped with a Dean & Stark apparatus surmounted by a reflux condenser and while sparging with nitrogen. The catalyst prepared in advance, acetic acid (0.92 ml) and piperidine (1.6 ml) in suspension in 3 ml of toluene, is added thereto. The mixture is brought to reflux with stirring for 9 hours and the water formed is removed via the Dean & Stark apparatus. Three further additions of the same amounts of catalyst were necessary. The cooled reaction mixture is poured into water and extracted with dichloromethane. The organic phase is washed with water, then dried and concentrated under reduced pressure. The reddish brown oil obtained is chromatographed on a silica column (eluent: Heptane/EtOAc 95:5). 37 g (Yield 50%) of the clean fractions of dimethyl 4-nitrobenzalmalonate are recovered in the form of a yellow oil which is used as is in the following stage.

Third Stage: Preparation of dimethyl 4-aminobenzalmalonate:

The derivative from the preceding stage (37 g, 0.072 mol) is dispersed in 30 ml of acetic acid and 45 ml of water while stirring and sparging with argon. The mixture is heated to 50° C. Iron (24.4 g, 0.437 mol) is added thereto portionwise without exceeding a temperature of 55° C. (introduction time 30 minutes). Subsequently, acetic acid (45 ml) is added dropwise without exceeding a temperature of 55° C. (introduction time 1 hour 30 minutes). The mixture is heated for a further 1 hour at 55° C. It is cooled, water is added and extraction is carried out twice with dichloromethane. The organic phase is washed with water, with a saturated sodium bicarbonate solution and with water and is then dried over sodium sulfate. After concentrating under reduced pressure, an orangey gum is obtained and is purified by passing through a silica column (eluent: Heptane/EtOAc 90:10). 8.6 g (Yield 25%) of the clean fractions of dimethyl 4-aminobenzalmalonate are recovered in the form of a yellow solid which is used as is in the following stage.

Fourth Stage: Synthesis of the Derivative of Example 7:

The intimately mixed mixture of the preceding product (2 g, $4.1 \times 10^{-3}$ mol), of 2,4-dichloro-6-(amyl 4'-aminobenzoate)-s-triazine (first stage of Example 2) (0.73 g, $2.05 \times 10^{-3}$ mol) and of sodium bicarbonate (0.34 g, $4.1 \times 10^{-3}$ mol) is left in a CEM Discover microwave system for 30 minutes at a temperature of 130-140° C. and under a power of 300 watts. The amorphous solid formed is extracted with dichloromethane. The organic phase is washed 3 times with water, is dried and is then concentrated under reduced pressure. The brown oil obtained is subjected to separation on a silica column (eluent: Heptane/EtOAc 80:20). Clean fractions in the form of a pale yellow powder of the derivative of Example 7 are recovered (0.5 g, Yield 16%):

UV (Ethanol):
$\lambda = 370$ nm, $E_{1\%} = 391$; $\lambda_{max} = 340$ nm, $E_{1\%} = 538$; $\lambda = 300$ nm, $E_{1\%} = 313$.

Example A

O/W Emulsion

| PHASES | INGREDIENTS | AMOUNTS (G %) |
|---|---|---|
| PHASE 1 | Glyceryl monostearate/polyethylene glycol (100 EO) stearate mixture | 1 |
| | Stearic acid | 1.5 |
| | Polydimethylsiloxane | 0.5 |
| | Cetyl alcohol | 0.5 |
| | Cetearyl glucoside/cetearyl alcohol mixture | 2 |
| | Preservative | 1 |
| | Triethanolamine | 0.45 |
| | $C_{12}/C_{15}$ Alkyl benzoate | 15 |
| | Compound of formula (1) | 1 |
| PHASE 2 | Ethylenediaminetetraacetic acid, disodium salt, $2H_2O$ | 0.1 |
| | Monopotassium monocetyl phosphate | 1 |
| | Glycerol | 5 |
| | Xanthan gum | 0.2 |
| | Deionized water (q.s.) | 68.35 |
| PHASE 3 | Acrylates/C10-30 alkyl acrylate crosspolymer | 0.2 |
| | Isohexadecane | 1 |
| PHASE 4 | Triethanolamine | 0.2 |
| | Deionized water | 1 |

Example B

O/W Emulsion

| PHASES | INGREDIENTS | AMOUNTS (G %) |
|---|---|---|
| PHASE 1 | Glyceryl monostearate/polyethylene glycol (100 EO) stearate mixture | 1 |
| | Stearic acid | 1.5 |
| | Polydimethylsiloxane | 0.5 |
| | Cetyl alcohol | 0.5 |
| | Cetearyl glucoside/cetearyl alcohol mixture | 2 |
| | Preservative | 1 |
| | Triethanolamine | 0.45 |
| | $C_{12}/C_{15}$ Alkyl benzoate | 15 |
| | Compound of formula (1) | 5 |
| PHASE 2 | Ethylenediaminetetraacetic acid, disodium salt, $2H_2O$ | 0.1 |
| | Monopotassium monocetyl phosphate | 1 |
| | Glycerol | 5 |
| | Xanthan gum | 0.2 |
| | Deionized water (q.s.) | 64.35 |
| PHASE 3 | Acrylates/C10-30 alkyl acrylate crosspolymer | 0.2 |
| | Isohexadecane | 1 |
| PHASE 4 | Triethanolamine | 0.2 |
| | Deionized water | 1 |

Example C

O/W Emulsion

| PHASES | INGREDIENTS | AMOUNTS (G %) |
|---|---|---|
| PHASE 1 | Glyceryl monostearate/polyethylene glycol (100 EO) stearate mixture | 1 |
| | Stearic acid | 1.5 |
| | Polydimethylsiloxane | 0.5 |
| | Cetyl alcohol | 0.5 |
| | Cetearyl glucoside/cetearyl alcohol mixture | 2 |
| | Preservative | 1 |
| | Triethanolamine | 0.45 |
| | $C_{12}/C_{15}$ Alkyl benzoate | 15 |
| | Compound of formula (1) | 1 |
| | Ethylhexyl methoxycinnamate | 3 |
| PHASE 2 | Ethylenediaminetetraacetic acid, disodium salt, $2H_2O$ | 0.1 |
| | Monopotassium monocetyl phosphate | 1 |
| | Glycerol | 5 |
| | Xanthan gum | 0.2 |
| | Deionized water (q.s.) | 65.35 |
| PHASE 3 | Acrylates/C10-30 alkyl acrylate crosspolymer | 0.2 |
| | Isohexadecane | 1 |
| PHASE 4 | Triethanolamine | 0.2 |
| | Deionized water | 1 |

Example D

O/W Emulsion

| PHASES | INGREDIENTS | AMOUNTS (G %) |
|---|---|---|
| PHASE 1 | Glyceryl monostearate/polyethylene glycol (100 EO) stearate mixture | 1 |
| | Stearic acid | 1.5 |
| | Polydimethylsiloxane | 0.5 |
| | Cetyl alcohol | 0.5 |
| | Cetearyl glucoside/cetearyl alcohol mixture | 2 |
| | Preservative | 1 |
| | Triethanolamine | 0.45 |
| | $C_{12}/C_{15}$ Alkyl benzoate | 15 |
| | Compound of formula (1) | 2 |
| | Ethylhexyl methoxycinnamate | 2 |
| PHASE 2 | Ethylenediaminetetraacetic acid, disodium salt, $2H_2O$ | 0.1 |
| | Monopotassium monocetyl phosphate | 1 |
| | Glycerol | 5 |
| | Xanthan gum | 0.2 |
| | Deionized water (q.s.) | 65.35 |
| PHASE 3 | Acrylates/C10-30 alkyl acrylate crosspolymer | 0.2 |
| | Isohexadecane | 1 |
| PHASE 4 | Triethanolamine | 0.2 |
| | Deionized water | 1 |

Example E

O/W Emulsion

| PHASES | INGREDIENTS | AMOUNTS (G %) |
|---|---|---|
| PHASE 1 | Glyceryl monostearate/polyethylene glycol (100 EO) stearate mixture | 1 |
| | Stearic acid | 1.5 |
| | Polydimethylsiloxane | 0.5 |
| | Cetyl alcohol | 0.5 |
| | Cetearyl glucoside/cetearyl alcohol mixture | 2 |
| | Preservative | 1 |
| | Triethanolamine | 0.45 |
| | $C_{12}/C_{15}$ Alkyl benzoate | 15 |
| | Compound of formula (1) | 3 |
| | Ethylhexyl methoxycinnamate | 1 |
| PHASE 2 | Ethylenediaminetetraacetic acid, disodium salt, $2H_2O$ | 0.1 |
| | Monopotassium monocetyl phosphate | 1 |
| | Glycerol | 5 |
| | Xanthan gum | 0.2 |
| | Deionized water (q.s.) | 65.35 |
| PHASE 3 | Acrylates/C10-30 alkyl acrylate crosspolymer | 0.2 |
| | Isohexadecane | 1 |
| PHASE 4 | Triethanolamine | 0.2 |
| | Deionized water | 1 |

Photostabilities Compared Between a Compound of the Prior Art and the Compound According to the Invention of Example 1

Products Tested:

2,4,6-Tris(diisobutyl 4'-aminobenzalmalonate)-s-triazine (Example 1 of Patent EP 0 507 691).

2,4-Bis(dineopentyl 4'-aminobenzalmalonate)-6-(butyl 4'-aminobenzoate)-s-triazine=compound of formula (1) according to the invention.

The two products were dissolved at 2% by weight in the oil Miglyol 812. Approximately 10 mg of oily solution are spread over 10 cm² at the surface of a hollow disc made of ground glass; the amount is determined by weighing.

The films of the oily solutions are irradiated for one hour using an Oriel solar simulator (UV-A=14.2 mW/cm²; UV-B=0.41 mW/cm²) and then extracted with 10 ml of ethanol comprising 10% of isopropanol subjected to ultrasound for 5 min. The products are quantified by analyzing the extracts by HPLC.

HPLC conditions: column: UP5WOD-25QS, 250×4.6 mm, 5 μm, Interchrom; eluent: methanol (Comparative Example 1) and 98% methanol+2% water (Example 1); flow rate: 1 ml/min; volume injected: 10 μl; detection: diode array detector; rt (min): 5.2 (compound of the prior art) and 7.4 (compound of Example 1).

The levels of loss are determined by comparison of the amounts of product present in the irradiated samples and in the non-irradiated controls prepared simultaneously and treated in the same way (means over 3 samples; A=area/mg of solution): % loss=100×(A0−Airr)/A0

Photostability Results:

| Compound | % of disappearance (mean loss) |
|---|---|
| Compound (prior art) | 10.0 |
| Compound of formula (1) (invention) | 4.6 |

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological photoprotective composition, comprising a thus effective amount of at least one s-triazine sunscreen compound formulated into a topically applicable, physiologically acceptable medium therefor, wherein the s-triazine sunscreen compound has the following structural formula (1):

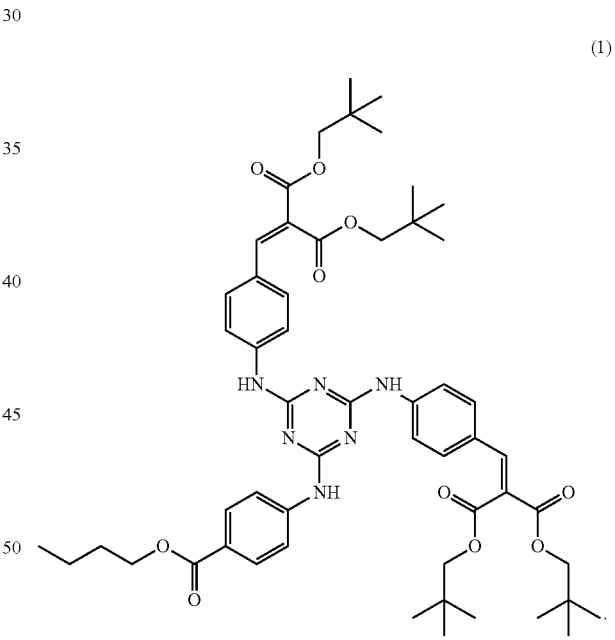

2. The cosmetic/dermatological photoprotective composition as defined by claim 1, said at least one s-triazine sunscreen compound comprising from 0.01% to 20% by weight thereof.

3. The cosmetic/dermatological photoprotective composition as defined by claim 1, said at least one s-triazine sunscreen compound comprising from 0.1% to 10% by weight thereof.

4. The cosmetic/dermatological photoprotective composition as defined by claim 1, further comprising at least one other sunscreen agent active in the UV-A and/or UV-B regions.

5. The cosmetic/dermatological photoprotective composition as defined by claim 1, further comprising at least one active agent for the artificial tanning and/or browning of the skin.

6. The cosmetic/dermatological photoprotective composition as defined by claim 1, further comprising at least one adjuvant selected from the group consisting of fatty substances, organic solvents, ionic or nonionic and hydrophilic or lipophilic thickeners, softeners, humectants, opacifiers, stabilizers, emollients, silicones, antifoaming agents, fragrances, preservatives, anionic, cationic, nonionic, zwitterionic or amphoteric surfactants, active principles, fillers, polymers, propellants or basifying or acidifying agents, and mixture thereof.

7. The cosmetic/dermatological photoprotective composition as defined by claim 1, formulated as a water-in-oil or oil-in-water emulsion.

8. The cosmetic/dermatological photoprotective composition as defined by claim 1, formulated as a makeup.

9. A method for photoprotecting a keratinous substance against damaging effects of UV-radiation, comprising topically applying thereon a thus effective amount of the cosmetic/dermatological composition as defined by claim 1.

10. The method as defined by claim 9, said keratinous substance comprising human skin, lips, nails, hair, eyelashes, eyebrows and/or scalp.

11. A method for controlling the variation in the color of the skin due to UV-radiation, comprising topically applying thereon a thus effective amount of the cosmetic/dermatological composition as defined by claim 1.

12. A compound of formula (I) shown below:

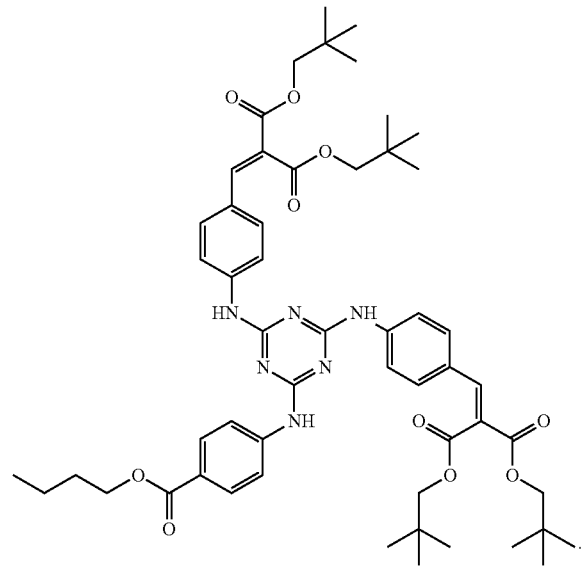

13. The topically applicable cosmetic/dermatological photoprotective composition as defined by claim 1, further comprising at least one s-triazine sunscreen compound formulated into a topically applicable, physiologically acceptable medium therefor, wherein the s-triazine sunscreen compound has the following structural formula (I):

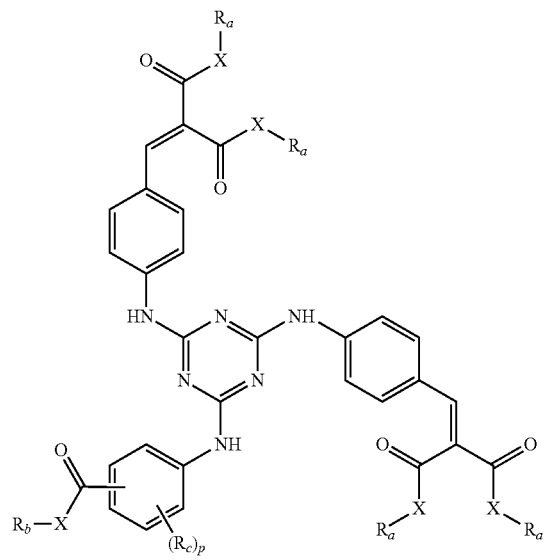

in which:

the radicals X, which may be identical or different, are each —O— or —$NR_6$—;

the radicals $R_a$, which may be identical or different, are each a radical of formula (II):

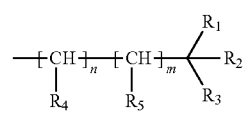

in which:

the radicals $R_1$ and $R_2$, which may be identical or different, are each a linear or branched $C_1$-$C_8$ alkyl radical, with the proviso that $R_1$ and $R_2$ can together form a $C_5$-$C_8$ ring member, optionally substituted by 1, 2 or 3 linear or branched $C_1$-$C_4$ alkyl radical(s), the radicals $R_3$, $R_4$ and $R_5$, which may be identical or different, are each a hydrogen atom or a linear or branched $C_1$-$C_4$ alkyl radical;

n has the value 0 or 1;

m has the value 0 or 1;

with the proviso that:

(i) when n=1 and $R_4$ is hydrogen, then m is equal to 0 and, (ii) when $R_1$ and $R_2$ together form a $C_5$-$C_8$ ring, then the sum n+m is other than 2;

the radical $R_6$ is hydrogen or a $C_1$-$C_8$ alkyl radical;

the radical $R_b$ is a linear or branched and optionally unsaturated $C_1$-$C_{20}$ alkyl radical, a $C_5$-$C_{12}$ cycloalkyl radical optionally substituted by 1 to 3 linear or branched $C_1$-$C_4$ alkyl radicals, the —($CH_2CHR_7$—O$)_q R_8$ radical or the —$CH_2$—CH(OH)—$CH_2$—O—$R_8$ radical;

the radical $R_7$ is hydrogen or methyl;

the radical $R_8$ is hydrogen or a $C_1$-$C_8$ alkyl radical;

q=1-20;

the $COXR_b$ group can be in the ortho, meta or para position with respect to the amino group;

the radical $R_c$ is a saturated or unsaturated and linear or branched $C_1$-$C_{20}$ alkyl radical, the OH radical or a linear or branched $C_1$-$C_{20}$ alkoxy radical; and p is equal to 0, 1 or 2;

with the further proviso that:

the compound of formula (I) is selected from the group consisting of (A), (B), (C), (D), and (E) defined below:

(A) (a) n=m=0 and
  (b) $R_1$, $R_2$ and $R_3$ are each methyl,
or $R_3$ is hydrogen and $R_1$ and $R_2$ together form a cyclohexyl ring;

(B) (a) n=1 and $R_4$ is an alkyl radical, or m=1 and $R_5$ is an alkyl radical, and
  (b) $R_1$ and $R_2$ are each a $C_1$-$C_4$ alkyl radical;

(C) (a) n=1 and $R_4$ is methyl, or m=1 and $R_5$ is methyl, and
  (b) $R_1$ and $R_2$ are each methyl;

(D) compound (2), (3), (4), (5), (9), or (10) shown below:

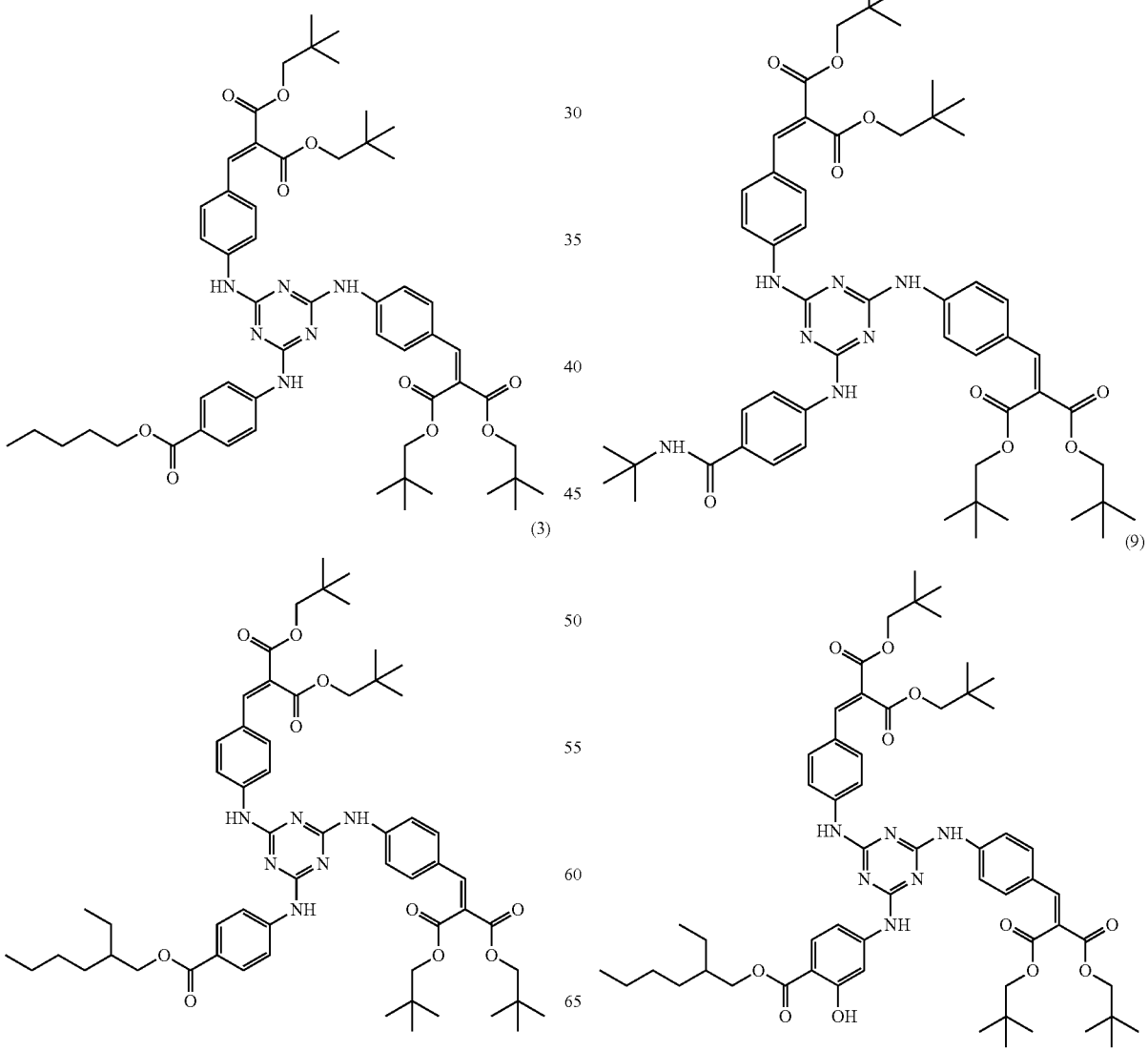

-continued
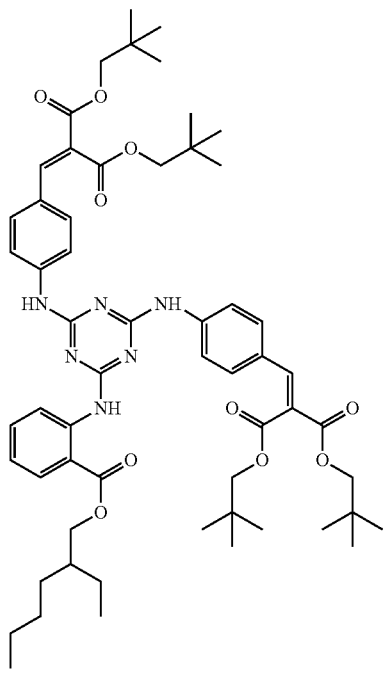
(E) compound (6) shown below:
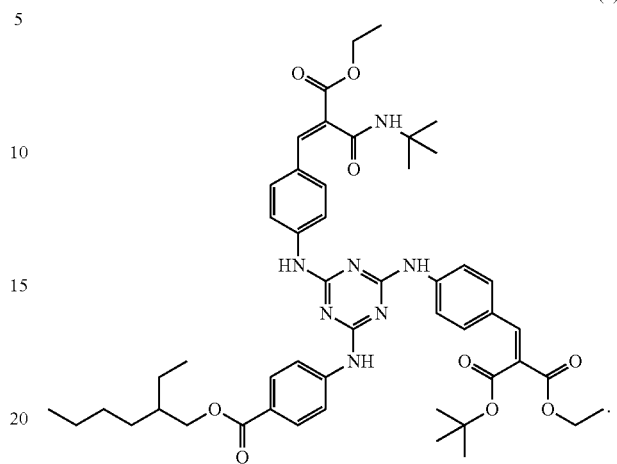
14. A topically applicable cosmetic/dermatological photoprotective composition, comprising a compound having the following structural formula (1):
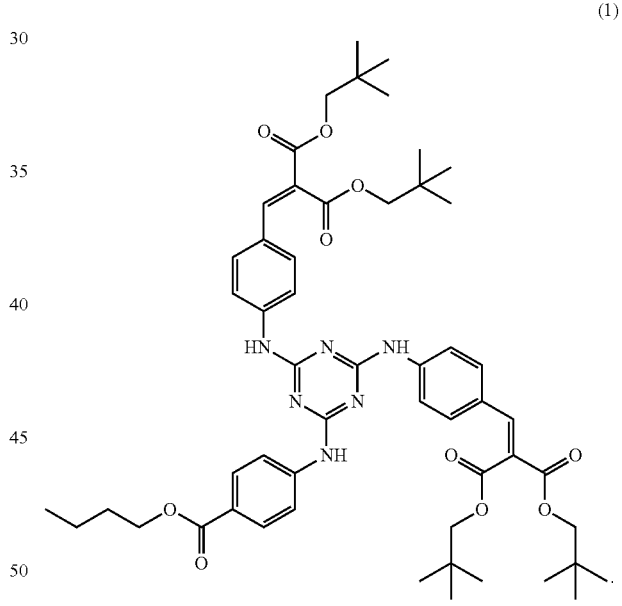
* * * * *